United States Patent [19]

Howells

[11] Patent Number: 4,474,982

[45] Date of Patent: Oct. 2, 1984

[54] 1-HALOMETHYL-2-ALKOXYETHYL ACRYLATES AND METHACRYLATES

[75] Inventor: Richard D. Howells, St. Paul, Minn.

[73] Assignee: Minnesota Mining and Manufacturing Company, St. Paul, Minn.

[21] Appl. No.: 433,970

[22] Filed: Oct. 13, 1982

[51] Int. Cl.$^3$ .......................................... C07C 69/653
[52] U.S. Cl. .................................. 560/223; 560/220; 560/221; 560/222; 526/243; 526/245; 526/273; 526/292.2; 526/292.3
[58] Field of Search ...................... 560/223, 22 D, 221, 560/222

[56] References Cited

U.S. PATENT DOCUMENTS

| | | | |
|---|---|---|---|
| 3,023,230 | 2/1962 | Baron et al. | 560/223 |
| 3,248,352 | 4/1966 | Marascia et al. | 524/487 |
| 3,282,905 | 11/1966 | Fasick et al. | 526/245 |
| 3,378,609 | 4/1968 | Fasick et al. | 525/227 |
| 3,462,296 | 8/1969 | Raynolds et al. | 525/200 |
| 3,491,169 | 1/1970 | Raynolds et al. | 525/160 |
| 3,645,990 | 2/1972 | Raynolds | 526/245 |
| 3,654,244 | 4/1972 | Pittman et al. | 526/243 |
| 3,838,104 | 9/1974 | Hayashi et al. | 526/243 |
| 4,013,627 | 3/1977 | Temple | 526/245 |
| 4,147,851 | 4/1979 | Raynolds | 526/245 |
| 4,296,224 | 10/1981 | Fukui et al. | 526/243 |

OTHER PUBLICATIONS

Rengel, G. L. and Young, R. C., "Internal Sizing of Paper and Paperboard", Tappi Monograph Series Number 33, pp. 170–189, (1971).

Colbert, Jerome F., "Fluorochemicals–Fluid Repellency for Nor-Woven Substrates", Tappi, The Journal of the Technical Association of the Pulp and Paper Industry, 59, (9) (Sep. 1976), pp. 129–131.

Banks, R. E., Ed., Organofluorine Chemicals and their Industrial Applications, pp. 231–234 (1979).

Schwartz, Craig, "Oil Resistance Utilizing Fluorochemicals", Tappi Conference Preprint, 1980 Sizing Short Course, Atlanta, Georgia, pp. 56–59.

Primary Examiner—Natalie Trousof
Assistant Examiner—L. Hendriksen
Attorney, Agent, or Firm—Donald M. Sell; James A. Smith; David R. Cleveland

[57] ABSTRACT

1-Halomethyl-2-alkoxyethyl acrylates and methacrylates useful for making acrylate and methacrylate polymers and copolymers. Preferred monomers are used to prepare fluorochemical copolymers which impart oil and water repellency to cellulosic materials and textile fibers. The fluorochemical copolymers are derived (by weight) from about 1 to 30% of the preferred monomers, 60 to 80% fluorochemical acrylate, 1 to 15% glycidyl acrylate or methacrylate, 1 to 6% of certain cationic acrylates or methacrylates, and 0 to 20% vinylidene chloride.

10 Claims, No Drawings

1-HALOMETHYL-2-ALKOXYETHYL ACRYLATES AND METHACRYLATES

TECHNICAL FIELD

This invention relates to monomers for use in making acrylate and methacrylate polymers and copolymers. This invention also relates to monomers for use in making fluorochemical copolymers which impart oil and water repellency to various substrates.

BACKGROUND ART

Various fluorochemical wet pick-up and internal sizing agents for paper treatment are described, for example, in Rengel and Young, "Internal Sizing of Paper and Paperboard", Tappi monograph series number 33, pp. 170–189 (1971), Colbert, "Fluorochemicals-Fluid Repellency for Non-woven Substrates", *Tappi, The Journal of the Technical Association of the Pulp and Paper Industry*, 59, 9, (September, 1976), Banks, Ed., *Organofluorine Chemicals and their Industrial Applications*, pp. 231–234 (1979), and Schwartz, "Oil Resistance Utilizing Fluorochemicals", Tappi conference preprint, 1980 Sizing Short Course, Atlanta, Ga. Several fluorochemical phosphates have been approved by the United States Food and Drug Administration for use on paperboard in direct contact with food for human consumption. These fluorochemical phosphates can be used as wet pick-up or as internal treatments. They primarily provide oil resistance, and are used on paper plates, bags for bakery goods, cartons and trays for oil fried foods (e.g., French fries), and in bags and cartons for pet foods.

The advent in recent years of the microwave oven has created a need for non-metallic containers for cooking or food-warming which have resistance to both oily and aqueous foods at oven temperatures, since metallic containers (e.g., aluminum trays) do not efficiently cook foods in microwave ovens and may promote electrical arcing if the metallic container walls approach or touch the walls of the microwave oven. A suitable non-metallic food container should also withstand freezing temperatures and conventional oven temperatures because foods sold in such containers will often be frozen and will be cooked in both microwave and conventional ovens. Cooking times for foods stored in such containers usually range from a few minutes to sixty minutes or more, and cooking temperatures usually range from about 95° C. to 240° C. or higher.

Existing commercially available fluorochemical phosphate sizing treatments do not provide sufficient high temperature water repellency to ovenable paperboard food trays exposed to cooking conditions for extended periods of time. Food packages have had to employ other container materials or constructions to obtain adequate ovenability. For example, formed food trays can be made entirely from plastics such as polyethylene terephthalate. Also, laminated, stamped food trays can be made from a layer of conventional paperboard coated on the food side with a thin (0.25 to 0.33 millimeters) film of extruded polyester. Food containers made entirely from plastic are relatively expensive, consume scarce petroleum resources, and lose rigidity at elevated temperatures. Food containers made from laminated paperboard and polyester sheets can become stained with oil on the unprotected outside surface (e.g., during food filling operations), are prone to rupture of the container at corners during tray-forming operations (due in part to differences in moisture content within the paperboard sheet), are susceptible to delamination when foods are heated to very high temperatures (e.g., when bacon or sausage are heated in microwave or conventional ovens), and are relatively expensive, requiring about 110 grams of polyester resin per kilogram of paperboard. In addition, scrap or waste paperboard from tray forming or other operations performed on paperboard/polyester laminate is not repulpable, and this scrap is sometimes as much as 25 percent of the total paperboard/polyester laminate consumed.

DISCLOSURE OF INVENTION

The present invention provides, in one aspect, novel monomers for use in making acrylate and methacrylate polymers and copolymers. The monomers of the invention are 1-halomethyl-2-alkoxyethyl acrylates or methacrylates. A preferred class of such monomers have the formula:

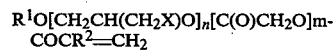

$$R^1O[CH_2CH(CH_2X)O]_n[C(O)CH_2O]_mCOCR^2{=}CH_2 \qquad I$$

wherein $R^1$ is a substituted or unsubstituted $C_{1-20}$ alkyl, cycloalkyl, or aralkyl group which can contain divalent catenary oxygen or sulfur atoms, $R^2$ is H or methyl, X is a halogen atom, n is 1 to about 10, and m is zero or 1.

DETAILED DESCRIPTION

In the practice of the present invention, the monomers of Formula I can be prepared using conventional methods. Monomers in which m is zero can be prepared, for example, by reacting an alcohol with epichlorohydrin, and reacting the resulting adduct with acryloyl chloride, methacryloyl chloride, acrylic acid, or methacrylic acid. Monomers in which m is 1 can be prepared, for example, by reacting the above-described adduct of alcohol and epichlorohydrin with chloroacetic acid, and combining the product of the latter reaction with acrylic acid or methacrylic acid. The above-described syntheses are generally carried out in the presence of suitable catalysts or acid acceptors, e.g., an acid catalyst for esterification with acrylic acid or methacrylic acid or a tertiary amine for esterification with acryloyl chloride or methacryloyl chloride. For any of the above-described syntheses, the final product can, if desired, be purified (e.g., by distillation, acid wash, or base wash) to remove residual acids, acid chlorides, catalysts, acid acceptors and other impurities or by-products.

The monomers of the present invention can be used to make acrylate or methacrylate polymers or copolymers using techniques known to those skilled in the art. The resulting polymers and copolymers can be cured using conventional techniques, (e.g., by free-radical polymerization, or by using ultraviolet radiation or electron beam curing) to form, for example, decorative or protective coatings or films, potting compounds, molding resins, adhesives, or sealants. The monomers of the present invention are less hydrophilic than corresponding non-halomethyl-containing monomers, and thus have particular utility for the making of polymers or copolymers in which reduced hydrophilicity is desired. The halomethyl group in the monomers of this invention can impart flame retardant properties and/or a site for attack by nucleophilic agents (e.g., crosslinking agents or reactive substrates), and the monomers of this invention are therefore useful for making polymers or copolymers where flame retardancy or susceptibility to reaction with nucleophilic agents is desired.

A preferred use for the monomers of this invention involves the making of fluorochemical copolymers, e.g. copolymers of the monomers of this invention with fluorinated monomers such as fluorochemical acrylates or methacrylates. A preferred subclass of the monomers of Formula I have been found which provide useful fluorochemical copolymers described in greater detail below. These fluorochemical copolymers impart high temperature oil and water repellency to cellulosic materials, or oil and water repellency to textile fibers, and comprise (by weight) about:

(a) 1 to 30% of polymer chain repeat units derived from halogenated alkyl or alkoxyalkyl acrylate monomer(s) of formula I, above, wherein $R^1$ is a $C_{1-20}$ alkyl, cycloalkyl, haloalkyl, or halocycloalkyl group, $R^2$ is H, and m is zero or 1;

(b) 60 to 80% of polymer chain repeat units derived from fluoroacrylate monomer(s) of the formula:

$$(R_f)_pQOCOCH=CH_2 \qquad II$$

wherein $R_f$ is a fluoroaliphatic radical-containing group having 3 to 20 carbon atoms, Q is a polyvalent organic connecting group, and p is 1 or 2;

(c) 1 to 15% of polymer chain repeat units derived from monomer(s) of the formula:

III wherein $R^3$ is H or methyl;

(d) 1 to 6% of polymer chain repeat units derived from cationic monomer(s) of the formula:

$$CH_2=C(R^4)ZY^+X^- \qquad IV$$

wherein $R^4$ is H or methyl, Z is a divalent electron-withdrawing group which activates free-radical polymerization, $Y^+$ is a monovalent cationogenic group, and $X^-$ is a water solubilizing anion; and (e) 0 to 20% of polymer chain repeat units derived from vinylidene chloride;

with the proviso that the weight percent of carbon-bonded fluorine in said copolymers is at least about 15%.

In the monomer of Formula I, $R^1$ is straight chain, branched, or cyclic, e.g., $CH_3(CH_2)_8CH_2-$, $CH_3(CH_2)_3-$, $CH_3CH_2-$, $CH_3$, $(CH_3)_2CHCH_2H_4-$, $(CH_3)_3C-$, $(CH_3)_2CH-$, $CH_3(CH_2)_4CH(C_2H_5)CH_2-$, $C_6H_{11}-$, $Cl(CH_2)_4-$, $Cl(CH_2)_3-$, $Cl(CH_2)_2-$, $ClCH_2CH(CH_2Cl)-$, $CH_3CH(CH_2Cl)-$, $CH_3CHClCH_2-$, $CH_3CH_2O(C_2H_4O)_5C_2H_4-$, $C_4H_9SC_3H_6-$, or $C_6H_5CH_2-$. $R^1$ preferably is a $C_{1-20}$ alkyl, cycloalkyl, haloalkyl, or halocycloakyl radical, more preferably is a $C_{1-5}$ alkyl radical, and most preferably is $CH_3-$ or $CH_3CH_2-$. $R^2$ preferably is H. Preferably X is chlorine. Preferably n is 1 to about 3, and most preferably n is 1. Preferably m is zero. Preferably, about 10 to 10 weight percent of the monomers of Formula I are used to form the above-described fluorochemical copolymers.

Representative monomers of Formula I include the acrylate monomers $CH_3OCH_2CH(CH_2Cl)OCOCH=CH_2$, $CH_3OCH_2CH(CH_2Cl)OC(O)CH_2OCOCH=CH_2$, $CH_3O[CH_2CH(CH_2Cl)O]_3$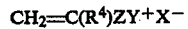$COCH=CH_2$, 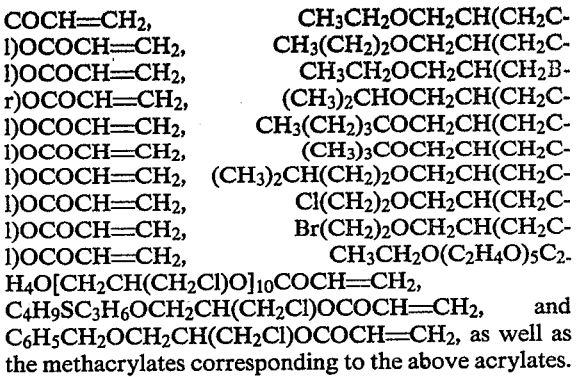$l)OCOCH=CH_2$, $l)OCOCH=CH_2$, $r)OCOCH=CH_2$, $l)OCOCH=CH_2$, $l)OCOCH=CH_2$, $l)OCOCH=CH_2$, $l)OCOCH=CH_2$, $l)OCOCH=CH_2$, $l)OCOCH=CH_2$, $H_4O[CH_2CH(CH_2Cl)O]_{10}COCH=CH_2$, $C_4H_9SC_3H_6OCH_2CH(CH_2Cl)OCOCH=CH_2$, and $C_6H_5CH_2OCH_2CH(CH_2Cl)OCOCH=CH_2$, as well as the methacrylates corresponding to the above acrylates.

The $R_f$ substituent of the monomers of Formula II, above is a monovalent, fluorinated, aliphatic, preferably saturated, organic radical having at least three carbon atoms and as many as twenty carbon atoms. The skeletal chain of $R_f$ can be straight, branched, or, if sufficiently large, cyclic, and can include catenary divalent oxygen atoms or trivalent nitrogen atoms bonded only to carbon atoms. Preferably, $R_f$ is fully fluorinated, but carbon-bonded hydrogen or chlorine atoms can be present as substituents on the skeletal chain of $R_f$, provided that not more than one atom of either hydrogen or chlorine is present for every two carbon atoms in the skeletal chain of $R_f$, and further provided that $R_f$ contains at least a terminal perfluoromethyl group. While $R_f$ radicals containing a large number of carbon atoms will function adequately, radicals containing not more than about 14 carbon atoms are preferred since larger radicals usually represent a less efficient utilization of fluorine that is possible with smaller radicals. Preferably, $R_f$ has an average of about 6 to 10 carbon atoms.

Q in Formula II, above is an organic polyvalent (e.g., divalent) acrylic or alicyclic radical of 1 to about 12 carbon atoms, or a polyvalent (e.g., divalent) aromatic radical of about 3 to 12 carbon atoms. Q can contain, for example, skeletal nitrogen, oxygen, or sulfur atoms, or carbonylimino, sulfonylimino, imino, or carbonyl radicals. Q is unsubstituted for substituted by halogen atoms, hydroxyl, alkyl, or aryl radicals, and preferably is free from aliphatic unsaturation. Suitable Q radicals include $-CH_2-$, $-C_2H_4-$, $-C_4H_8-$, $-C_6H_4-$, $-C_6H_3<$, $-CH_2C_6H_4CH_2-$, $-C_2H_4SC_2H_4-$, $-C_2H_4OC_4H_8-$, $-CH_2OC_2H_4-$, $-SO_2N(R^5)C_2H_4-$, $-CON(R^5)(C_2H_4)$, $-C_3H_6CON(R^5)C_2H_4-$, $-C_2H_4N(R^5)C_2H_4-$, $-COOCH_2C(CH_3)_2CH-$, $-SO_2N(R^5)CH_2CH(CH_3)-$, and $-C_2H_4SO_2N)R^5)C_4H_8-$, wherein $R^5$ is H or a $C_1$-alkyl radical. Preferably, Q is $-CH_2-$, $-C_2H_4-$, or $-SO_2N(R^5)C_2H_4-$.

Preferably, the monomers of Formula II contain at least about 30 weight percent fluorine and more preferably about 40 to 60 weight percent fluorine. Preferably, about 65 to 75 weight percent of the monomers of Formula II are used to form the above-mentioned fluorochemical copolymers.

Representative monomers of Formula II include $C_8F_{17}SO_2N(CH_3)CH_2CH_2OCOCH=CH_2$, $C_6F_{13}C_2H_4SC_2H_4OCOCH=CH_2$, $C_2F_5C_6F_{10}CH_2OCOCH=CH_2$, $C_7F_{15}CH_2OCOCH=CH_2$, $C_7F_{15}CON(CH_3)C_2H_4OCOCH=CH_2$, $(CF_3)_2CF(CF_2)_6CH_2CH(OH)CH_2OCOCH=CH_2$, $(CF_3)_2CFOC_2F_4C_2H_4OCOCH=CH_2$, $C_8F_{17}C_2H_4SO_2N(C_3H_7)C_2H_4OCOCH=CH_2$, $C_7F_{15}C_2H_4CONHC_4H_8OCOCH=CH_2$,

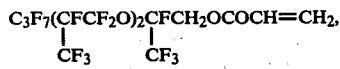

$C_8F_{17}SO_2N(C_2H_5)C_4H_8OCOCH=CH_2$,
$(C_3F_7)_2C_6H_3SO_2N(CH_3)C_2H_4OCOCH=CH_2$,

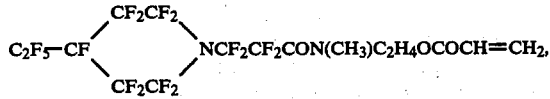

$C_8F_{17}CF=CHCH_2N(CH_3)C_2H_4OCOCH=CH_2$.

In the monomers of Formula III, above, $R^3$ preferably is methyl. Preferably, about 3 to 10 weight percent of the monomers of Formula III are used to form the above-mentioned fluorochemical copolymers.

In the monomer of Formula IV, above, the Z group has a carbonyl or aromatic group or an oxygen or sulfur atom bonded directly to the vinylidene group of the monomer. The Z group can be, for example, $-COO(CH_2)_p-$, $-CO(CH_2)_p-$, $-CONH(CH_2)_p-$, $-OCO(CH_2)_p-$, $-O(CH_2)_p-$, $-S(CH_2)_p-$, $-C_6H_4-$, or $-C_6H_4(CH_2)_p-$, where p is 1 to 10. The polymethylene moiety $-(CH_2)_p-$ and the aromatic moiety $-C_6H_4-$ in such structures can be substituted with substituent groups or atoms which do not interfere with free-radical polymerization, such as alkyl, aryl, or hydroxyl groups or halogen atoms. The $R^4$ group preferably is $CH_3-$. The Z group preferably is selected from $-COOCH_2CH(OH)CH_2-$, $-COO(CH_2)_k-$, or $-CONH(CH_2)_k-$, where k is 2 to 6. Useful $Y^+$ groups include (a) the pyridinium ion

(b) the ion $N^+(R^6)_3$ where each $R^6$ independently is H or a $C_{1-4}$ alkyl group, or where any two of $R^6$ combine to form an alkylene group having 4 to 5 chain carbon atoms, or any two of $R^6$ are $-(CH_2)_2-$ and combine with an oxygen atom to form the moiety $-(CH_2)_2O(CH_2)_2-$, (c) phosphonium ions, and (d) sulfonium ions. Preferably, $Y^+$ is $N^{30}$ $(R^7)_3$ where each $R^7$ independently is a $C_{1-4}$ alkyl group. The anion $X^-$ is a matter of choice, and ordinarily is selected based upon the method of synthesis of the cationic monomer. $X^-$ preferably is selected fron halide ions such as $Cl^-$, $Br^-$, $I^-$, and alkyl sulfate ions such as $CH_3OSO_3^-$. Preferably, about 2 to 4 weight percent of the monomers of Formula IV are used to form the above-described fluorochemical copolymers.

Representative monomers of Formula IV include $CH_2=C(CH_3)COOC_2H_4N^+(CH_3)_3$ $Cl^-$,
$CH_2=CHCOOC_2H_4N^+(CH_3)_3$ $Cl^-$,
$CH_2=C(CH_3)COOC_2H_4N^+(CH_3)_3$ $-OSO_3CH_3$,
$CH_2=C(CH_3)COOCH_2CH(OH)CH_2N^+(CH_3)_3$ $Cl^-$,
$CH_2=C(CH_3)CONHC_3H_6N^+(CH_3)_3$ $Cl^-$,
$CH_2=C(CH_3)COOC_2H_4N^+(C_2H_5)_2H$ $Cl^-$,

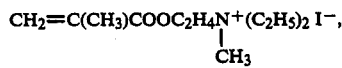

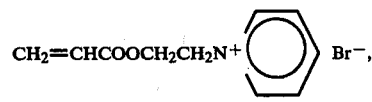

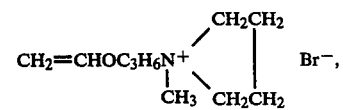

and $CH_2=CHC_6H_4CH_2N^+(CH_3)_3$ $Cl^-$.

Many of the above-described fluorochemical copolymers provide commercially useful water repellency immediately after application thereof to cellulosic materials. In contrast, fluorochemical copolymers made by batch processes and derived from a non-halomethyl-containing monomer in place of the monomer of Formula I, above, do not provide commercially useful water repellency immediately after application thereof to cellulosic materials. Instead, when the latter fluorochemical copolymers are applied to cellulosic materials, aging (by heating for a few minutes or more at elevated temperature or by equilibration for a few days or more at ambient temperature) generally is required to obtain commercially useful water repellency.

The performance of paperboard, or of textile fibers, which have been treated with the above-described fluorochemical copolymers is affected, in part, by the types and amounts of monomers from which such fluorochemical copolymers are derived. For example, use of increased amounts of the monomers of Formula I or Formula II tends to enhance oil and water repellency of the treated paperboard or textile fiber. Use of increased amounts of the monomer of Formula III tends to enhance water repellency, but can detract from oil repellency. Use of increased amounts of the monomer of Formula IV tends to enhance efficient deposition of the fluorochemical copolymer onto cellulosic or textile fibers. Also, this latter monomer aids in emulsifying the fluorochemical copolymer and in stabilizing the emulsion in which the copolymer can be prepared, thereby enabling the use of reduced levels of other emulsifiers. Vinylidene chloride, if used, tends to enhance water repellency, and serves as a compatible "filler" monomer in the fluorochemical copolymer. Where higher weight percentages of the monomer of Formula I are used, then lesser amounts of vinylidene chloride are required, enabling the amount of vinylidene chloride to be reduced to zero if desired.

Minor, non-interfering amounts of monomers other than those described above can also be incorporated into the fluorochemical copolymers. For example, the fluorochemical copolymers can contain up to about 10 weight percent of polymer units derived from ethylene, vinyl acetate, vinyl chloride, vinyl fluoride, vinylidene fluoride, vinyl chloroacetate, acrylonitrile, vinylidene cyanide, styrene, alkyl styrenes, halogenated styrenes, methacrylonitrile, N-vinylcarbazole, vinylpyridine, vinyl alkyl ethers, vinyl alkyl ketones, butadiene, chloroprene, fluoroprene, isoprene, and mixtures thereof.

Non-interfering amounts of, for example, alkyl or alkoxyalkyl methacrylates, fluorochemical methacrylates, fluorochemical alkoxyalkylmethacrylates, acids such as acrylic acid, methacrylic acid, or chloroacetic acid (most particularly acrylic acid), or hydroxyl containing vinyl monomers (particularly those containing terminal hydroxyl functionality, such as N-methylolacrylamide and 2-hydroxyethyl acrylate) can be incorporated into the fluorochemical copolymers, but the use thereof preferably is avoided, as their presence in the fluorochemical copolymers detracts from the oil and water repellency, or delays the attainment of commercially acceptable water repellency, for paperboard or textile fiber treated therewith.

The fluorochemical copolymers can be prepared using known techniques for emulsion or solution polymerization. In order to prepare treated paperboard, the fluorochemical copolymers preferably are applied as internal (i.e., "wet-end") additives to an aqueous suspension of cellulosic fibers, using conventional papermaking equipment and techniques known to those skilled in the art of papermaking. The fluorochemical copolymer is added to the furnish in amounts sufficient to provide the desired level of oil and water repellency. In general, these amounts are between about 0.2 to 2 percent fluorochemical copolymer based on weight of fibers. For reasons of economy, it is preferred to employ a low level of fluorochemical copolymer, coincident with attainment of adequate oil and water repllency in the finished paperboard product. Following addition of the fluorochemical copolymer, the furnish is processed using conventional papermaking technology.

Treated paperboard can also be prepared by applying the fluorochemical copolymers using wet pick-up methods, such as a size press or calendar stack. If desired, sequential internal and wet pick-up application of the fluorochemical copolymers can be employed.

Some treated paperboard made using fluorochemical copolymers derived from monomers of the present invention attains maximum water repellency after aging (see, e.g., the treated paperboard of copolymer Example 10, below). Little or no aging will be required for many other fluorochemical copolymers exemplified below.

The fluorochemical copolymer-treated paperboard can be formed into containers (e.g., trays) using conventional techniques (e.g., the "Sprinter", "Kliclok", "Peerless", or molded pulp methods). Because internally-applied fluorochemical copolymers penetrate uniformly throughout the paper web, aggressive die stamping, folding, or creasing of the treated paperboard will not expose untreated fibers, and the oil and water repellency of the treated paperboard will not be materially lessened by tray-forming operations. Also, if a moisturizing step is used during container-forming, the treated paperboard will have a more uniform moisture content than moisturized paperboard/polyester laminates, enabling the treated paperboard to be more readily formed into containers without rupture thereof. In contrast to the use of paperboard/polyester laminates, the fluorochemical copolymer-treated paperboard does not tend to stick to the heated steel dies used in press-forming tray manufacturing operations. Both sides of the fluorochemical copolymer-treated paperboard readily receive printing ink. In contrast, it is difficult to perform printing operations upon the polyester side of paperboard/polyester laminates. In addition, scrap fluorochemical copolymer-treated paperboard which is left over from the container-forming operation can be repulped and reused, unlike scrap from container-forming operations employing paperboard/polyester laminates.

The treated paperboard containers can be filled with food and stored using conventional techniques. Cooking of food in such containers is also carried out in conventional fashion, but the elevated high temperature oil and water repellency of the paperboard containers will enable use of high temperatures (e.g., 230° C.), long cooking times (e.g., two hours or more), and cooking of foods (e.g., spinach) which have been prone to cause oil or water staining in paperboard containers heretofore employed.

The above-described fluorochemical copolymers have also been found to be useful for imparting soil resistance and oil and water repellency to textiles (e.g., polyester carpet fibers). The fibers (or yarn) can be treated as such or in an aggregated form (e.g., skein or roving) with the fluorochemical copolymer, or the fabricated textile (e.g., articles such as carpet and woven fabrics) can be treated with the fluorochemical copolymer. The treatment can be carried out by applying the fluorochemical copolymer by known techniques customarily used in applying fluorochemicals to fibrous substrates. For textile application dependent on substantial exhaustion of the fluorochemical copolymer from the treating medium, the concentration of copolymer in the exhaustion bath generally will be about 0.001 to 0.1 weight percent. For applications not involving exhaustion, e.g., padding, spraying, etc., higher concentrations will be needed. The amount of fluorochemical copolymer deposited on the treated textile irrespective of the particular mode of application will be, functionally speaking, sufficient to impart the desired degree of oil and water repellency, and generally this amount will be 0.02 to 3, preferably 0.06 to 0.16 weight percent, or, expressed in terms of fluorine content, 0.01 to 1.5, preferably 0.03 to 0.08 weight percent fluorine.

The following examples are offered to aid understanding of the present invention and are not to be construed as limiting the scope thereof.

MONOMER EXAMPLE 1

Alcohol Preparation

In a 1 liter 3-neck flask equipped with a condenser, addition funnel, thermometer, mechanical stirrer, and electric heating mantle were placed 276 g (6.0 moles) ethanol and 3.5 g $SnCl_4$. The resulting reaction mixture was heated with stirring to 55° C., the heating mantle was removed, and 462.5 g (5.0 moles) epichlorohydrin was added dropwise to the flash over a 3 hour period while maintaining the reaction temperature at about 55° to 60° C. After completion of the addition, stirring was continued for about 1 hour. Gas chromatographic analysis of a portion of the reaction mixture indicated a yield of about 90 weight % of $C_2H_5OCH_2CH(CH_2Cl)OH$ and about 9 weight % of $C_2H_5O[CH_2CH(CH_2Cl)O]_2H$. A solution of 5 g $Na_2CO_3$ in 12 ml water was added to the flask. Excess ethyl alcohol and water were distilled from the reaction mixture. The reaction mixture remaining in the flask was filtered to yield about 660 g mixed chloromethyl alcohols. The pure monochloromethyl alcohol $C_2H_5OCH_2CH(CH_2Cl)OH$ was obtained by distillation (b.p. 65°–70° C. at 2 torr).

Acrylate Preparation

In a 500 ml flask equipped as described above (but unheated) were placed 69.2 g (0.5 mole) distilled $C_2H_5OCH_2CH(CH_2Cl)OH$, 100 g $CH_2Cl_2$, 70.7 g (0.7 mole) triethylamine, and 0.015 g monomethyl ether of hydroquinone. To the resulting mixture was added dropwise, over a one hour period with stirring, a solution of 63.3 g (0.7 mole) acryloyl chloride in 100 g $CH_2Cl_2$. The temperature of the reaction mixture was allowed to rise to about 35° C. during the acryloyl chloride addition. The reaction mixture was stirred for about 30 minutes at ambient temperature, and 120 ml water was added to the flask followed by addition of a solution of about 5 g NaHCO$_3$ in 25 ml water. The phases were separated and the organic phase was washed twice with 50 ml portion of dilute aqueous NaCl solution. The organic phase was dried over anhydrous MgSO$_4$, concentrated under aspirator vacuum, and the residual acrylate product distilled. The product had a boiling point of 48°–53° C. at 0.2 torr, and was identified by IR and NMR spectroscopy as C$_2$H$_5$OCH$_2$CH(CH$_2$Cl)OCOCH=CH$_2$. Gas chromatographic analysis indicated a purity of 98.7%.

MONOMER EXAMPLES 2–11

Using the general procedure of Monomer Example 1, several additional monomers were prepared. For Monomer Example 9, an alcohol was prepared using methanol in place of ethanol in the Alcohol Preparation step of Monomer Example 1, the resulting chloromethyl alcohol was reacted with a 20 percent molar excess of chloroacetic acid in heptane, water was removed from the reaction mixture by azeotropic distillation, and the resulting product was identified as having the general formula:

$$R^1O[CH_2CH(CH_2X)O]_nC(O)CH_2Cl \qquad V$$

where R$^1$ is methyl, X is chlorine and n is 1. The monomer of Formula V was next reacted with acrylic acid in the presence of triethylamine to form the desired monomer. For Monomer Example 10, the general procedure of Monomer Example 1 was followed but methacryloyl chloride was substituted for acryloyl chloride in the Acrylate Preparation step. In Monomer Example 11, the general procedure of Monomer Example 1 was followed but a 4:3 molar ratio of epichlorohydrin to methanol was used in the Alcohol Preparation step.

Set out below in Table A are the monomer produced and, where measured, boiling points for the monomers of Monomer Examples 2 through 11.

TABLE A

| Monomer Example | Monomer | Boiling point, °C. (torr) |
|---|---|---|
| 2 | CH$_3$OCH$_2$CH(CH$_2$Cl)OCOCH=CH$_2$ | 53–54 (0.5) |
| 3 | CH$_3$C$_2$H$_4$OCH$_2$CH(CH$_2$Cl)OCOCH=CH$_2$ | 55–60 (0.2) |
| 4 | (CH$_3$)$_2$CHOCH$_2$CH(CH$_2$Cl)OCOCH=CH$_2$ | 60–64 (0.2) |
| 5 | CH$_3$C$_3$H$_6$OCH$_2$CH(CH$_2$Cl)OCOCH=CH$_2$ | 71–75 (0.2) |
| 6 | (CH$_3$)$_3$COCH$_2$CH(CH$_2$Cl)OCOCH=CH$_2$ | 56–62 (0.2) |
| 7 | (CH$_3$)$_2$CHC$_2$H$_4$OCH$_2$CH(CH$_2$Cl)OCOCH=CH$_2$ | 77–80 (0.2) |
| 8 | ClC$_2$H$_4$OCH$_2$CH(CH$_2$Cl)OCOCH=CH$_2$ | 80–85 (0.2) |
| 9 | CH$_3$OCH$_2$CH(CH$_2$Cl)OC(O)CH$_2$OCOCH=CH$_2$ | 98–107 (0.4) |
| 10 | CH$_3$OCH$_2$CH(CH$_2$Cl)OCOC(CH$_3$)=CH$_2$ | 52–55 (0.2) |
| 11 | CH$_3$O[CH$_2$CH$_2$CH(CH$_2$Cl)O]$_{1-3}$COCH=CH$_2$ | — |

Several monomers of the invention were used to prepare fluorochemical copolymers. The fluorochemical copolymers were applied to cellulosic materials or to textile fibers, and the oil and water repellency of the resulting substrates was evaluated, as shown in the Copolymer Examples set forth below.

COPOLYMER EXAMPLE 1

Preparation of Copolymer Emulsion

The following ingredients were placed in a screw-capped, 115 ml glass bottle, in the amounts set forth below in Table I:

TABLE I

| Ingredient | Amount, g |
|---|---|
| C$_8$F$_{17}$SO$_2$N(CH$_3$)C$_2$H$_4$OCOCH=CH$_2$ | 21.0 |
| C$_2$H$_5$OCH$_2$CH(CH$_2$Cl)OCOCH=CH$_2$ | 5.4 |
| 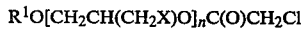CH$_2$CHCH$_2$OCOC(CH$_3$)=CH$_2$ | 1.5 |
| CH$_2$=C(CH$_3$)COOC$_2$H$_4$N$^+$(CH$_3$)$_3$ Cl$^-$ [a] | 1.2 |
| n-Octanethiol | 0.06 |
| C$_{18}$H$_{37}$N$^+$(CH$_3$)(C$_2$H$_4$O)$_x$H(C$_2$H$_4$O)$_y$H Cl$^-$, x + y = 15 [b] | 0.9 |
| 2,2'-Azobis(isobutyramidine) dihydrochloride [c] | 0.15 |
| Deionized water | 52.5 |
| Acetone, reagent grade | 17.5 |

[a]"Sipomer Q-6-75", commercially available from Alcolac, Inc.
[b]"Ethoquad 18/25", commercially available from Armak Industrial Chemical Division of Akzona, Inc.
[c]"V50", commercially available from Crescent Chemical Co.

The glass bottle and its contents were briefly subjected to reduced pressure to remove oxygen. The glass bottle was then flushed with oxygen-free nitrogen, sealed, placed in a water bath maintained at 72° C., and tumbled for 16 hours. A 95 percent yield of fluorochemical copolymer was obtained as an aqueous emulsion containing about 29 percent solids.

COPOLYMER EXAMPLE 2

Preparation of Fluorochemical Copolymer-treated Paperboard

A 390 gram mixture of bleached sulfate wood pulp containing equal parts of "Alberta HiBrite" softwood pulp and "Marathon" hardwood pulp was placed in a 0.68 kg "Voith" laboratory beater apparatus with 23 liters of water. The resulting mixture was refined for 80 minutes to yield a pulp having a Canadian Standard Freeness of 450 to 500, as measured according to TAPPI Standard No. T227-05-58. The refined wood pulp suspension was then diluted with an equal volume of water to form a suspension containing about 0.8 percent by weight solids. The diluted suspension was stirred with an electric mixer, and 1250 ml of the stirred mixture (containing about 10 g of refined fiber) was removed and placed in a 2 liter graduated cylinder. A 0.15 g portion of cationic polymeric retention aid ("Betz 1275", commercially available from Betz Laboratories Inc.) was mixed with the contents of the graduated cylinder. Next, 0.12 g (0.04 g on a solids basis) of the fluorochemical copolymer of Copolymer Example 1 was added to the graduated cylinder, followed by mixing. The resulting fiber suspension was poured into a 30.5 cm × 30.5 cm paper handsheet mold having an 80 mesh stainless steel screen (commercially available from Williams Apparatus Co.) and containing 10 liters of water. The perforated stirrer was moved up and down 3 times to mix the fiber suspension and water, and the mold then drained. The screen, wet handsheet and two paper blotters were pressed using a hand roller. The screen was removed from the sheet, two paper blotters were placed on the wire side of the sheet, and the resulting assembly was squeezed in a hydraulic press at a pressure of 6.9 MPa. The pressed handsheet was dryed in a 46 cm×51 cm sheet dryer (commercially available from Williams Apparatus Co.) that had been set at an initial temperature of 150° C. After insertion of the pressed handsheet, the temperature of the metal dryer plate decreased to about 100° C. The handsheet was removed after the plate temperature recovered to 120° C. and cut into thirds. One third was formed into a tray and evaluated using the procedure described below. Another third was aged by heating in a forced air oven (commercially available from Despatch Oven Co.) at 120° C. for 15 minutes, and the remaining third was aged by equilibrating at 22° C., 50% R.H. for 14 days. Each third of the handsheet sample was cut into 12.7 cm×12.7 cm square sheets. The square sheets were folded into square trays each having 2.5 cm deep sidewalls and a 7.7 cm×7.7 cm base.

The treated handsheet samples were evaluated for oil repellency by filling two of each of the trays with corn oil ("Mazola", commercially available from Best Foods division of CPC International, Inc.) and placing the filled trays (and enough other filled test trays to bring the total number of filled test trays to 20) on a single oven rack in a preheated 204° C. electric oven for 30 minutes. Such temperatures and times exceed those generally used to evaluate existing fluorochemical oligomer-treated paperboard. The heated trays were removed, emptied, and inspected on the outer surfaces of the sides, base, and corner creases for staining. The oil repellency of the treated handsheets was evaluated visually according to the following scale:

0=staining after trays filled and before tray heated
1=very heavy staining (of sides, bottom and creases)
2=heavy staining (mainly of bottom and creases)
3=moderate staining (mainly of creases)
4=staining of creases only
5=no staining.

The treated handsheet samples were evaluated for water repellency by filling two each of the treated trays with 1 percent aqueous sodium chloride solution and placing the trays (and enough other filled test trays to bring the total number of filled test trays to 20) in a 204° C. electric oven for 30 minutes. The trays were removed and emptied, and evaluated for staining using the above criteria.

Set out below in Table II are the oil and water repellency ratings obtained for each of the above-described handsheet samples.

TABLE II

| | Repellency rating | |
|---|---|---|
| Handsheet sample | Corn Oil | Aqueous NaCl |
| not aged | — | 4 |
| aged at 120° C. for 15 min. | 4.5 | 5 |
| aged at 22° C., 50% R.H. for 14 days | 4.5 | 4.5 |

The copolymer of Copolymer Example 1 was used to prepare additional handsheets with dimensions of 30.5 cm×30.5 cm×0.58 mm, containing about 30 g refined treated fiber. The handsheets were unaged, and were formed into trays as described above. Various commercial canned or frozen food products containing oily or aqueous fluids were placed in the trays. The food-filled trays were heated in a conventional oven and the trays then evaluated for staining using the above-described criteria. Set out below in Table III are the food type, cooking conditions, and repellency ratings obtained.

TABLE III

| | Cooking conditions[2] | | Repellency |
|---|---|---|---|
| Food[1] | Temp. | Time | rating |
| Spinach[3] | 204° C. | 30 min. | 4 |
| Spinach[4] | 204° C. | 30 min. | 2 |
| Green beans[5] | 204° C. | 30 min. | 4.5 |
| Green beans[6] | 204° C. | 30 min. | 5 |
| Beef gravy[7] | 204° C. | 30 min. | 5 |
| Lasagna[8] | 190° C. | 30 min. | 4.8 |
| Fried chicken[8] | 190° C. | 30 min. | 5 |
| Pudding[8] | 190° C. | 30 min. | 5 |

[1]Frozen foods were thawed before being placed in trays.
[2]Cooked in a conventional oven ("Kenmore" model 911.9337910 electric range, commercially available from Sears, Roebuck and Co.) at the indicated temperature and time.
[3]"Libby's" canned spinach, commercially available from Libby McNeil & Libby, Inc.
[4]"Bird's Eye" frozen chopped spinach, commercially available from Bird's Eye Co.
[5]"Green Giant" canned sliced green beans, commercially available from Pillsbury Co.
[6]"Green Giant" frozen cut green beans in butter sauce, commercially available from Pillsbury Co.
[7]"Franco-American" canned beef gravy, commercially available from Campbell Soup Co.
[8]"Swanson", commercially available from Campbell Soup Co.

This example shows that fluorochemical copolymers derived from monomers of this invention provide excellent oil and water repellency on paperboard, under both laboratory and actual food cooking conditions.

COMPARATIVE EXAMPLE 1

Using the method of Copolymer Examples 1 and 2, but using the monomer $C_2H_5OCH_2CH(CH_3)OCOCH=CH_2$ in place of the monomer $C_2H_5OCH_2CH(CH_2Cl)OCOCH=CH_2$, a fluorochemical copolymer was prepared, exhausted onto cellulose fiber, made into paperboard, and evaluated. The treated paperboard exhibited an initial water repellency of 1.5, a water repellency after aging of 4.5, and an oil repellency after aging of 4.5.

This comparative example shows that substitution of a non-halomethyl-containing monomer for the monomer of Formula I provided a fluorochemical copolymer with low initial water repellency.

COPOLYMER EXAMPLES 3 to 10

Using the methods of Copolymer Examples 1 and 2, several fluorochemical copolymers were prepared, exhausted onto cellulose fiber, made into paperboard, and evaluated both without aging and with aging at 120° C. in a forced air oven for fifteen minutes. Set out below in Table IV are the copolymer charging ingredients and amount in grams of each ingredient for each Copolymer Example. Set out below in Table V are the percent loading of fluorochemical copolymer solids on fiber, amount and type of retention aid, and oil and water repellency ratings for paperboard treated with the fluorochemical copolymers of Table IV.

These Copolymer Examples show the use of various monomers of Formula I to prepare fluorochemical copolymers.

TABLE IV

| Copolymer charging ingredients | Copolymer Example no. and amount in grams | | | | | | | |
|---|---|---|---|---|---|---|---|---|
| | 3 | 4 | 5 | 6 | 7 | 8 | 9 | 10 |
| $C_8F_{17}SO_2N(CH_3)C_2H_4OCOCH=CH_2$ | 21 | 21 | 21 | 21 | 21 | 21 | 21 | 21 |
| $CH_3OCH_2CH(CH_2Cl)OCOCH=CH_2$ | 5.4 | | | | | | | |
| $CH_3C_2H_4OCH_2CH(CH_2Cl)OCOCH=CH_2$ | | 5.4 | | | | | | |
| $(CH_3)_2CHOCH_2CH(CH_2Cl)OCOCH=CH_2$ | | | 5.4 | | | | | |
| $CH_3C_3H_6OCH_2CH(CH_2Cl)OCOCH=CH_2$ | | | | 5.4 | | | | |
| $(CH_3)_3COCH_2CH(CH_2Cl)OCOCH=CH_2$ | | | | | 5.4 | | | |
| $(CH_3)_2CHC_2H_4OCH_2CH(CH_2Cl)OCOCH=CH_2$ | | | | | | 5.4 | | |
| $ClC_2H_4OCH_2CH(CH_2Cl)OCOCH=CH_2$ | | | | | | | 5.4 | |
| $CH_3OCH_2CH(CH_2Cl)OC(O)CH_2OCOCH=CH_2$ | | | | | | | | 5.4 |
| 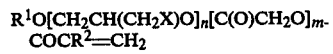 $CH_2CHCH_2OCOC(CH_3)=CH_2$ (with epoxide O) | 1.5 | 1.5 | 1.5 | 1.5 | 1.5 | 1.5 | 1.5 | 1.5 |
| $CH_2=C(CH_3)COOC_2H_4N^+(CH_3)_3Cl^-$ | 1.2 | 1.2 | 1.2 | 1.2 | 1.2 | 1.2 | 1.2 | 1.2 |
| $N_2[C(CH_3)_2C(NH_2)=NH \cdot HCl]_2$ | 0.15 | 0.15 | 0.15 | 0.15 | 0.15 | 0.15 | 0.15 | 0.15 |
| $C_{18}H_{37}N^+(CH_3)(C_2H_4O)_xH(C_2H_4O)_yH\ Cl^-$, $x + y = 15$ | 0.9 | 0.9 | 0.9 | 0.9 | 0.9 | 0.9 | 0.9 | 0.9 |
| $n\text{-}C_8H_{17}SH$ | 0.06 | 0.06 | 0.06 | 0.06 | 0.06 | 0.06 | 0.06 | 0.06 |
| Water | 52.5 | 52.5 | 52.5 | 52.5 | 52.5 | 52.5 | 52.5 | 52.5 |
| Acetone | 17.5 | 17.5 | 17.5 | 17.5 | 17.5 | 17.5 | 17.5 | 17.5 |

TABLE V

| | Copolymer Example No. | | | | | | | |
|---|---|---|---|---|---|---|---|---|
| | 3 | 4 | 5 | 6 | 7 | 8 | 9 | 10 |
| % Copolymer on fiber | 0.4 | 0.4 | 0.4 | 0.4 | 0.4 | 0.4 | 0.4 | 0.4 |
| Retention aid, % on fiber | | | | | | | | |
| [a] Polymeric cationic aliphatic amide | 2.0 | 1.5 | 1.5 | 2.0 | 2.0 | 1.5 | 2.0 | 2.0 |
| Repellency rating | | | | | | | | |
| Corn oil after aging | 4.8 | 4.3 | 4.1 | 4.3 | 1 | 3.5 | 5 | 4.8 |
| Aqueous NaCl before aging | 4.5 | 4.5 | 4.3 | 4.5 | 4 | 4.8 | 4.3 | 3.5 |
| Aqueous NaCl after aging | 5 | 4.8 | 4.9 | 5 | 4.5 | 5 | 5 | 5 |

[a] "Betz 1275", commercially available from Betz Laboratories, Inc.

COPOLYMER EXAMPLE 11

To evaluate the utility as a textile treatment of a fluorochemical copolymer derived from a monomer of this invention, a loosely knitted fabric of carrierless polyester staple carpet yarn (12 denier per filament) was treated with a padding bath containing 0.74 wt. % of the fluorochemical copolymer of Copolymer Example 1, to provide 0.22% solids on fiber. The treated fabric was dried for 15 minutes at 160° C., disperse dyed using a "Launder-Ometer" laboratory dyeing machine (Model LEF, commercially available from the Atlas Electric Devices Company), and dried for 10 minutes at 130° C. The treated fabric was found to have an oil repellency rating of 3 as measured using AATCC Standard Test 118-1978 (modified by waiting 10 seconds instead of 30 seconds before measuring oil repellency). The aqueous stain repellency of the treated fabric was measured using a water/isopropyl alcohol test. In such test, aqueous stain repellency is expressed in terms of the "WATER/IPA" rating of the treated fabric. Treated fabrics which are penetrated by or resistant only to a 100% water/0% isopropyl alcohol mixture, the least penetrating of the test mixtures, are given a rating of 100/0, whereas treated fabrics resistant to a 0% water/100% isopropyl alcohol mixture, the most penetrating of the test mixtures, are given a rating of 0/100. Other intermediate values are determined by use of other water/isopropyl alcohol mixtures, in which the percentage amounts of water and isopropyl alcohol are each multiples of 10. The WATER/IPA rating corresponds to the most penetrating mixture which does not penetrate or wet the fabric after 10 seconds contact. In general, a WATER/IPA rating of $<50/>50$ is desirable. The treated fabric of this example had a WATER/IPA rating of 40/60.

The resistance of the treated fabric to loss of performance during dyeing was evaluated by measuring the fluorine content of the treated fabric before and after dyeing. The treated fabric had 756 ppm fluorine before dyeing and 743 ppm fluorine after dyeing, indicating that nearly 100 percent of the fluorochemical copolymer was retained on the fabric after dyeing.

Various modifications and alterations of this invention will be apparent to those skilled in the art without departing from the scope and spirit of this invention and the latter should not be restricted to that set forth herein for illustrative purposes.

What is claimed is:

1. A compound having the formula:

$$R^1O[CH_2CH(CH_2X)O]_n[C(O)CH_2O]_mCOCR^2=CH_2$$

wherein $R^1$ is a halosubstituted $C_{1\text{-}20}$ alkyl or a halosubstituted or unsubstituted $C_{1\text{-}20}$ cycloalkyl or aralkyl group which can contain divalent catenary oxygen or sulfur atoms, $R^2$ is H or methyl, X is a halogen atom, n is 1 to about 10, and m is zero or 1.

2. A compound according to claim 1, wherein $R^1$ is a $C_{1\text{-}20}$ cycloalkyl, haloalkyl, or halocycloalkyl group and $R^2$ is H.

3. A compound according to claim 1, wherein $R^1$ is a $C_{1\text{-}5}$ haloalkyl radical.

4. A compound according to claim 1, wherein $R^2$ is H.

5. A compound according to claim 1, wherein X is chlorine.

6. A compound according to claim 1, wherein n is 1 to about 3.

7. A compound according to claim 1, wherein m is zero.

8. A compound having the formula:

$$R^1O[CH_2CH(CH_2X)O]_nC(O)CH_2OCOCR^2=CH_2$$

wherein $R^1$ is a halosubstituted or unsubstituted $C_{1\text{-}20}$ alkyl, cycloalkyl, or aralkyl group which can contain divalent catenary oxygen or sulfur atoms, $R^2$ is H or methyl, X is a halogen atom, and n is 1 to about 10.

9. The compound R¹O[CH₂CH(CH₂Cl)O]₁₋₃C(O)CH₂OCOCH=CH₂ according to claim 8, wherein R¹ is CH₃— or CH₃CH₂—.

10. A compound having the formula:

R¹O[CH₂CH(CH₂X)O]$_n$[C(O)CH₂O]$_m$COCR²=CH₂ wherein R¹ is a halosubstituted or unsubstituted $C_{1-20}$ alkyl, cycloalkyl, or aralkyl group which can contain divalent catenary oxygen or sulfur atoms, R² is H or methyl, X is a halogen atom, n is 3 to about 10, and m is zero or 1.

* * * * *

UNITED STATES PATENT AND TRADEMARK OFFICE
CERTIFICATE OF CORRECTION

PATENT NO. : 4,474,982
DATED : October 2, 1984
INVENTOR(S) : Richard D. Howells

It is certified that error appears in the above-identified patent and that said Letters Patent is hereby corrected as shown below:

Col. 1, line 54, "packages" should read --packagers--.

Col. 3, line 51, "$CH_3 13,$" should read --$CH_3-,$--.

Col. 3, line 62, "10" (2rd occurrence) should read --20--.

Col. 4, line 42, "for" should read --or--.

Col. 4, line 51, "$C_{1-}$" should read --$C_{1-4}$--.

Col. 5, line 48, "$N^{30}$" should read --$N^+$--.

Col. 15, line 1, "$R^1O[CH_2CH(CH_2Cl)O[_{1-3}C(O)C-$" should read
-- $R^1O[CH_2CH(CH_2Cl)O]_{1-3}C(O)C-$ --.

*Signed and Sealed this*

*Twenty-fourth* Day of *September 1985*

[SEAL]

Attest:

Attesting Officer

DONALD J. QUIGG

Commissioner of Patents and
Trademarks—Designate